United States Patent
Bowers et al.

(10) Patent No.: US 11,980,705 B2
(45) Date of Patent: May 14, 2024

(54) OXYGENATION SYSTEM

(71) Applicant: Spectrum Medical Ltd., Gloucester (GB)

(72) Inventors: Scott Bowers, Gloucester (GB); Stephen Turner, Gloucester (GB); Jeremy Tamari, Gloucester (GB)

(73) Assignee: SPECTRUM MEDICAL LTD., Gloucester (GB)

( * ) Notice: Subject to any disclaimer, the term of this patent is extended or adjusted under 35 U.S.C. 154(b) by 925 days.

(21) Appl. No.: 16/976,428

(22) PCT Filed: Mar. 1, 2019

(86) PCT No.: PCT/GB2019/050579
§ 371 (c)(1),
(2) Date: Aug. 27, 2020

(87) PCT Pub. No.: WO2019/166823
PCT Pub. Date: Sep. 6, 2019

(65) Prior Publication Data
US 2021/0113755 A1 Apr. 22, 2021

(30) Foreign Application Priority Data

Mar. 2, 2018 (GB) .................................. 1803400
Nov. 6, 2018 (GB) .................................. 1818112

(51) Int. Cl.
*A61M 1/16* (2006.01)
*A61M 1/36* (2006.01)

(52) U.S. Cl.
CPC ......... *A61M 1/1698* (2013.01); *A61M 1/3623* (2022.05); *A61M 2202/0225* (2013.01);
(Continued)

(58) Field of Classification Search
CPC .............. A61M 1/1698; A61M 1/3623; A61M 2202/0225; A61M 2202/0266;
(Continued)

(56) References Cited

U.S. PATENT DOCUMENTS 4,440,722 A 4/1984 Luppi
4,493,692 A 1/1985 Reed
(Continued)

FOREIGN PATENT DOCUMENTS

CN 2216835 Y 1/1996
CN 2738809 Y 11/2005
(Continued)

OTHER PUBLICATIONS

International Searching Authority. International Search Report and Written Opinion for application PCT/GB2019/050579. dated May 24, 2019. 13 pages.
(Continued)

*Primary Examiner* — Benjamin J Klein
(74) *Attorney, Agent, or Firm* — QUARLES & BRADY LLP

(57) ABSTRACT

An oxygenator (10) for an extracorporeal ventilation system comprises a gas passage and a blood passage arranged to allow gas exchange of an oxygenation gas supply with blood via a gas-blood interface (34). The gas passage leads from a gas inlet zone (28) via the gas-blood interface (34) to a gas exhaust zone (40). The blood passage leads from a blood inlet (12) via the gas-blood interface (34) to a blood outlet (14). The oxygenator comprises a supply gas distribution arrangement (26, 28A, 28B). This allows the oxygenation gas supply to be modulated differently for different interface regions of the gas-blood interface. The oxygenator can be used to remove or reduce the formation of gaseous microemboli bubbles.

24 Claims, 8 Drawing Sheets

(52) U.S. Cl.
CPC ............... *A61M 2205/3334* (2013.01); *A61M 2230/202* (2013.01); *A61M 2230/205* (2013.01); *A61M 2230/50* (2013.01)

(58) Field of Classification Search
CPC .... A61M 2205/3334; A61M 2230/202; A61M 2230/205; A61M 2230/50
See application file for complete search history.

(56) References Cited

U.S. PATENT DOCUMENTS

| | | | |
|---|---|---|---|
| 4,749,551 A | | 6/1988 | Borgione |
| 4,874,581 A | | 10/1989 | Sutherland |
| 2014/0216252 A1 | * | 8/2014 | Joost ................... A61M 1/1698 96/6 |
| 2016/0015881 A1 | * | 1/2016 | Utsugida ............. A61M 1/3666 422/48 |
| 2019/0160217 A1 | * | 5/2019 | Marseille ............. B01D 63/026 |
| 2020/0188571 A1 | * | 6/2020 | Gipson ............... A61M 1/3666 |

FOREIGN PATENT DOCUMENTS

| | | |
|---|---|---|
| CN | 102036701 A | 4/2011 |
| CN | 107405441 A | 11/2017 |
| EP | 0249308 A2 | 12/1987 |
| GB | 2437254 A | 10/2007 |
| GB | 2561221 A | 10/2018 |
| GB | 2563062 A | 12/2018 |
| JP | H04193178 A | 7/1992 |
| JP | 2001079083 A | 3/2001 |
| JP | 2004160217 A | 6/2004 |
| WO | 1991016967 A1 | 11/1991 |
| WO | 2013005193 A2 | 1/2013 |
| WO | 2016071691 A1 | 5/2016 |
| WO | 2016087859 A1 | 6/2016 |
| WO | 2016087861 A1 | 6/2016 |
| WO | 2016181189 A1 | 11/2016 |
| WO | 2017211460 A1 | 12/2017 |
| WO | 2018026672 A1 | 2/2018 |
| WO | 2019035869 A1 | 2/2019 |

OTHER PUBLICATIONS

Intellectual Property Office. Search Report for application GB1803400.9. dated Aug. 9, 2018. 3 pages.

* cited by examiner

```
50
```

| | |
|---|---|
| 52 | Provide an oxygenator gas-blood interface separated into regions that are separately supplyable by sweep gas |
| 54 | Supply sweep gas to at least one region |
| 56 | Modulate sweep gas differently for each region |
| 58 | Modulate area of gas-blood interface region(s) |
| 60 | Monitor PaO2 and PaCO2 of outgoing blood |
| 62 | Modulate total gas flow rate |
| 64 | Provide veno-arterial shunt to bypass gas-blood interface |
| 66 | Mix venous blood with oxygenator-treated blood |

Fig. 15

OXYGENATION SYSTEM

CROSS REFERENCE TO RELATED APPLICATIONS

This application represents the U.S. national stage entry of PCT/GB2019/050579 filed Mar. 1, 2019, which claims benefit of United Kingdom application 1803400.9 filed Mar. 2, 2018 and United Kingdom application 1818112.3 filed Nov. 6, 2018. The contents of these applications are hereby incorporated by reference as set forth in their entirety herein.

FIELD OF THE INVENTION

The present invention relates to an oxygenation system and to a method for extracorporeal blood oxygenation and carbon dioxide control while limiting the formation of gaseous microemboli bubbles (GME), as well as providing conditions that favour elimination of GME. In particular, the present invention relates to an oxygenation system and method of providing conditions that remove and/or reduce the formation of GME.

BACKGROUND

Extracorporeal perfusion is a process in which blood from a patient is circulated outside the patient's body, to be re-oxygenated and to have its carbon-dioxide levels adjusted, in order to be in a condition to be returned to the patient or to be used for exclusively extracorporeal testing purposes in which the blood is not returned to a patient. More specifically, venous (oxygen-reduced) blood is supplied via an incoming line, or venous line, to an oxygenator in which the blood is oxygenated by exposure to an oxygenation gas in an oxygenator for supply via an outgoing line, or arterial line, back to the patient as arterial blood.

Extracorporeal perfusion is typically used to substitute heart and lung functionality during a medical procedure, eg open heart surgery or lung treatment. Extracorporeal blood is in that case brought into a condition for subsequent return to the patient. Blood conditioning includes setting an appropriate temperature, flow rate, line pressure, and mixing with agents such as anti-coagulants. With regard to the oxygen content and carbon dioxide content, this is adjusted in the oxygenator, where blood is exposed to an oxygenation gas via a gas-blood interface through which oxygen is permitted to diffuse into and to be taken up by the blood. The gas-blood interface may be provided by gas-permeable walls of hollow fibres, where gas passes through the inner passage of the hollow fibres, and blood around the outside of the hollow fibres. After blood has left the oxygenator, there is usually no further possibility to increase the blood oxygen content before the blood is administered to a patient. To provide an illustration of the flow rates involved, in adult patients, blood may be circulated at a typical flow rate in the region of 5 litres per minute (lpm). For this and other reasons, many parameters must be controlled to ensure that the blood leaving the oxygenator is appropriately oxygenated and carbon dioxide levels are appropriate.

International patent application PCT/GB2015/053694 by the present applicant, published as WO2016/087859, the contents of which are incorporated by reference, discloses an oxygenation system for a ventilation system comprising a flow control arrangement for controlling the flow rate of the exhaust gas relative to the oxygenation gas. WO2016/087859 also discloses a blender for preparing an oxygenation gas with a high-accuracy oxygen content at low flow rates. The blender and flow control arrangement disclosed in WO2016/087859 can be used to maintain low flow rates of an oxygenation gas while also permitting a high degree of blending accuracy and while permitting the exhaust gas to be withdrawn at an appropriate flow rate that is low, yet higher than the oxygenation gas supply.

As stated in WO2016/087859, even though vacuum may be employed to assist with a controlled exhaust gas removal at low flow rates, the gas flow within the oxygenator is achieved at atmospheric pressure, because the oxygenator housing comprises at its exhaust side openings to avoid pressurisation at the exhaust side of the oxygenator, to avoid a positive pressure gradient from exhaust side (outlet) to oxygenation gas inlet. A significant outlet-to-inlet pressure gradient could lead to the introduction of gross volumes of gas across the gas-blood interface (typically constituted by gas-permeable gas-exchange fibres), which in turn could lead to gas bubbles forming in the blood, which render the blood unsafe for return to a patient.

Great British patent application GB1705556.7 by the present applicant, published as GB2561221A, discloses an oxygenator design capable of maintaining hypobaric (sub-atmospheric) pressure conditions while still complying with emergency pressure-relief requirements, by providing a pressure-isolated oxygenator housing comprising a safety mechanism against over-pressurisation. Hypobaric pressure conditions reduce the formation of gas bubbles in the blood.

The present invention is concerned with providing additional options for blood oxygenation during extracorporeal perfusion.

SUMMARY OF THE INVENTION

In accordance with a first aspect of the invention, there is provided an oxygenator as defined by claim 1.

The oxygenator is for an extracorporeal ventilation system and comprises a gas passage and a blood passage arranged to allow gas exchange of an oxygenation gas supply with blood via a gas-blood interface, wherein the gas passage leads from a gas inlet zone via the gas-blood interface to a gas exhaust zone. The blood passage leads from a blood inlet via the gas-blood interface to a blood outlet.

The oxygenator comprises a supply gas distribution arrangement allowing the oxygenation gas supply to be modulated differently for different interface regions of the gas-blood interface. The different interface regions are arranged successively in blood flow direction for blood directed through the gas-blood interface to pass each interface region and the gas-blood interface is uniformly distributed within the blood passage.

The gas-blood interface may be provided in the form of an arrangement in which the interface structure, such as bundle of hollow fibres, is held together by so-called potting. The hollow fibres provide gas passages from the gas inlet zone through the gas-blood interface to the gas exhaust zone. The potting is provided at either end of the hollow fibres and provides two wall structures as boundaries for the blood passage. One wall is located at the inlet-facing side of the fibres, between the gas inlet zone and the gas-blood interface, and another wall at the outlet-facing side of the fibres, between the gas-blood interface and the gas exhaust zone. The area between the potting may be considered an interface chamber within which blood may pass around the hollow fibres, while oxygenation gas passes within the hollow fibres.

The supply gas is understood to be oxygenation gas, which is also referred to as "sweep" gas. The sweep gas is supplied initially to the gas inlet zone from where the gas can then pass into the many different openings of the hollow fibres that make up the gas-blood interface. By "supply gas distribution arrangement", a structure or mechanism is meant that allows the supply gas to be distributed differently to different regions of the gas-blood interface. Different arrangements to achieve this are described in more detail below; such arrangements may include multiple supply gas inlets each supplying a different region of the gas inlet zone and/or physical separations, as well as moveable separators to provide gas inlet compartments or controllable flow-diverters to direct gas flow.

The gas-blood interface within the blood passage is uniformly distributed, and extends practically continuously across different interface regions, by which is meant that there are no noticeable interruptions or voids between different interface regions, such that blood cells passing through the blood passage experience practically the same flow conditions regardless of whether they pass through or between different interface regions, as if the blood passage leads through a single interface region.

In some embodiments, the supply gas distribution arrangement comprises one or more partitions each dividing the gas inlet zone in a plurality of gas inlet sections, each section having a border with a different region of the gas-blood interface.

In some embodiments, the supply gas distribution arrangement comprises one or more partitions each dividing the gas-blood interface in a plurality of gas-blood interface compartments.

The border can be imagined to correspond to an area of the potting in contact with the gas inlet zone. The partitions allow each section to be supplied by supply gas of different flow rate and/or composition. Thereby, different gas transition conditions are provided for each section between the gas inlet zone and the interface chamber. Likewise, the partitions may separate the gas-blood interface. A partition may extend from the gas inlet zone into the gas-blood interface, and may extend through the gas-blood interface.

In some embodiments, the blood passage through the gas-blood interface comprises a circular or oval profile and/or wherein the blood passage through the gas-blood interface is linear.

A circular or oval profile reduces and practically avoids corners or dead regions in which flow conditions might otherwise encourage clotting. A linear blood passage improves homogenous flow conditions across the gas-blood interface.

At least one partition may be movable to adjust the size of the border between a gas inlet section and the gas-blood interface.

The partition may be a translatable wall, or a pivotable wall, such as a gas-flow diverting flap.

At least one partition may be in contact with an outer wall of the gas-blood interface.

For instance, the outer wall of the gas-blood interface may be constituted by a potting surface that constitutes a boundary of the interface chamber.

In some embodiments, the gas passage extends linearly.

This allows the gas exhaust zone to be positioned opposite, or practically opposite the gas inlet zone.

In some embodiments, the gas-blood interface arrangement comprises hollow fibres comprising gas passage openings toward the gas inlet zone.

In some embodiments, the oxygenator comprises a mechanism allowing openings of one or more hollow fibres, or of one or more groups of hollow fibres, to be individually closed and/or opened.

This may be achieved by a lid function or shutter function configured to block part or all of the gas passage openings of the hollow fibres. The lid or shutter may be in contact with the potting surface.

In some embodiments, the supply gas distribution arrangement comprises a flow-diverter capable of re-directing the flow. The flow-diverter is controllable by a control system. The control-system may include a closed loop control to modulate the flow-diverter to achieve desired flow properties through the gas-blood interface.

In some embodiments, the supply gas distribution arrangement comprises a plurality of gas inlet ports each suitable for a supplying oxygenation gas to the gas inlet zone.

This allows oxygenation gas with different properties to be provided, for instance, with different flow rates and/or with different composition.

In some embodiments, a separate inlet port is provided for each gas inlet section.

In some embodiments, the oxygenator comprises a blood sensor arrangement to obtain measurements representative of one or more blood values selected from a group comprising of incoming blood oxygen concentration, incoming blood carbon dioxide concentration, outgoing blood oxygen concentration, outgoing blood carbon dioxide concentration, and blood temperature.

In some embodiments, the oxygenator comprises a gas sensor arrangement to obtain measurements representative of one or more gas values selected from a group comprising of oxygenation gas flow rate, oxygenation gas pressure, exhaust gas flow rate, exhaust gas pressure, exhaust gas oxygen concentration, and exhaust gas carbon dioxide concentration.

In some embodiments, the oxygenator comprises a supply gas control system configured to receive the one or more measurements representative of one or more blood values or one or more gas values, and to modulate the flow rate and/or the composition of the oxygen gas supply gas in response to the measurements.

The sensors, coupled with a mechanism controlling the flow rate and/or composition of the gas and or blood, respectively, allow a closed loop control to modulate the supply gas and blood stream to maintain a specific property, such as PaO2, PaCO2, and/or temperature, at a predetermined set point.

An exemplary closed loop control mechanism is described in international patent application PCT/GB2015/053697 by the present applicant, published as WO2016/087861, the contents of which are incorporated by reference.

The present gas distribution arrangement provides another mechanism for altering gas properties by being able to modulate the gas composition, flow rates, and/or regions of the gas-blood interface to be utilised in order to maintain a blood property at a set point. By "maintaining" a property, it is meant that the system is responsive to compensate gas parameters (flow, composition, interface area) to thereby compensate for temporary fluctuations.

In some embodiments, the oxygenator comprises a veno-arterial shunt providing a diversion from the blood inlet to the blood outlet, the diversion bypassing the gas-blood interface, wherein the veno-arterial shunt allows a portion of incoming blood to be diverted to the blood outlet without exposure to the oxygenation gas supply.

In some embodiments, the oxygenator comprises a shunt flow controller to control the amount of incoming blood diverted to bypass the gas-blood interface.

In some embodiments, the oxygenator is configured to receive one or more measurements representative of one or more blood values and/or gas values, and to actuate the shunt flow controller to modulate the flow rate of blood diverted through the shunt passage in response to the measurements.

In some embodiments, the oxygenator is comprised in an extracorporeal ventilation system comprising one or more oxygenation gas supply lines each connected to the supply gas distribution arrangement.

DESCRIPTION OF THE FIGURES

Exemplary embodiments of the invention will now be described with reference to the Figures, in which:

FIG. 15 shows steps of a sequence of an oxygenation method.

DESCRIPTION

Figure 1:
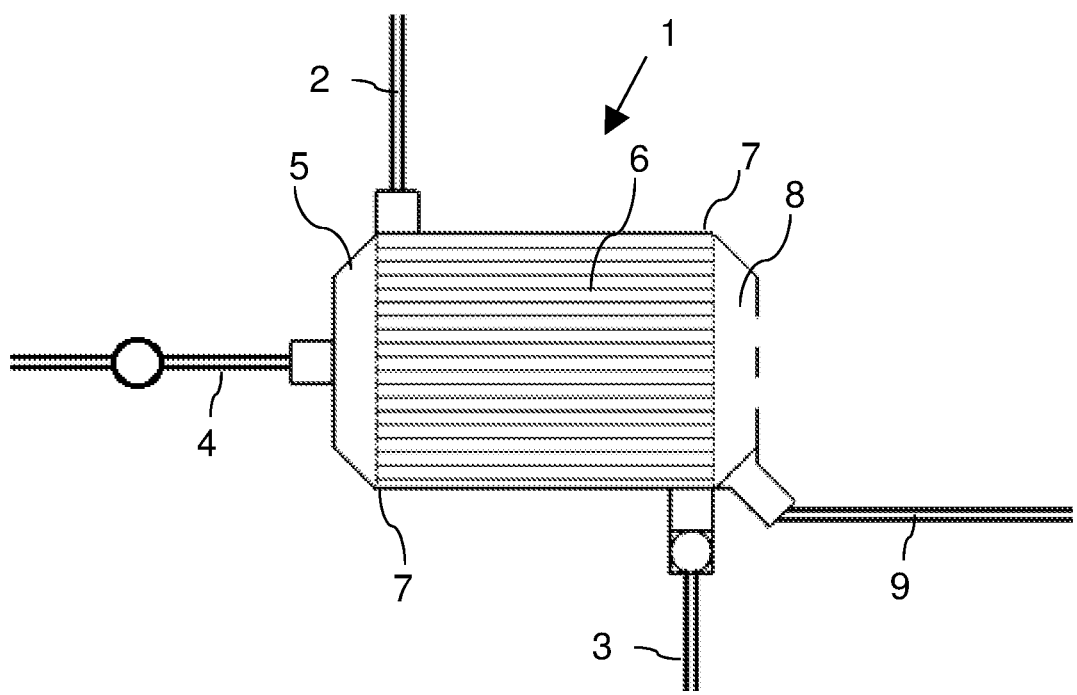
FIG. 1 shows a prior art oxygenator arrangement.

FIG. 1 shows elements expected to be found in a known oxygenator 1 used in extracorporeal ventilation. The oxygenator 1 is provided to expose oxygen-reduced, or venous, blood to a gas supply comprising oxygen thereby to allow a gas exchange between the blood and the gas supply in which the blood is oxygenated and carbon dioxide is removed in order to provide oxygen-enriched arterial blood. The oxygenator 1 comprises a blood passage comprising blood inlet 2 via which venous blood is supplied into the oxygenator 1 and a blood outlet 3 via which outgoing blood leaves the oxygenator 1 for further use, often as arterial blood to be returned to a patient but also for purely extracorporeal testing purposes. The oxygenator 1 also comprises a gas passage comprising a sweep gas supply 4 leading via an inlet chamber 5 through a gas-blood interface 7 and via an exhaust chamber 8 to an exhaust passage 9.

Modern gas-blood interfaces typically comprise a bundle of several thousand hollow, micro-porous fibres with micro-porous, gas-permeable properties. The sweep gas is supplied through the interior, hollow space of the fibres and blood flows around the fibres; and gas exchange is promoted by relative diffusion gradients between the concentrations of oxygen and carbon dioxide in blood and gas, respectively. The hollow fibres are held together at their ends by so-called potting 7 which seals off the blood passage from the inlet chamber 5 and the exhaust chamber 8. The design is such that the gas flow conditions, in particular flow rate and volumes, from the inlet chamber 5 through the gas-blood interface 6 are, as much as is controllable, expected to be homogeneous, as would be expected from a single, static gas supply port. It will be understood that, in operation, the gas composition and pressure will change along the hollow fibres from the inlet-facing potting 7 towards outlet-facing potting 7, because the oxygen content is gradually reducing as blood picks up oxygen molecules, and the carbon dioxide content is gradually increasing due to diffusion from blood carbon dioxide into the oxygenation gas. However, for a given distance from the inlet chamber 5, the gas flow conditions of the hollow fibres are similar and practically homogeneous.

The aim of such an oxygenator type is to modulate the partial pressure of oxygen PaO2 in the outgoing blood. The aim may also be to modulate the partial pressure of carbon dioxide PaCO2 in the outgoing blood. PaO2 may be modulated by adjusting the oxygen percentage (ie partial oxygen pressure) of the oxygenation gas, the remaining component being mainly nitrogen. PaCO2 may be modulated by adjusting the flow rate of the oxygenation gas. Using an oxygenation gas supply system such as described in WO2016/087859 and WO2016/087861 by the present applicant, both the composition and the flow rate of the oxygenation gas can be controlled simultaneously, allowing both the PaO2 and PaCO2 that is expected in the outgoing blood to be modulated simultaneously.

Figure 2:
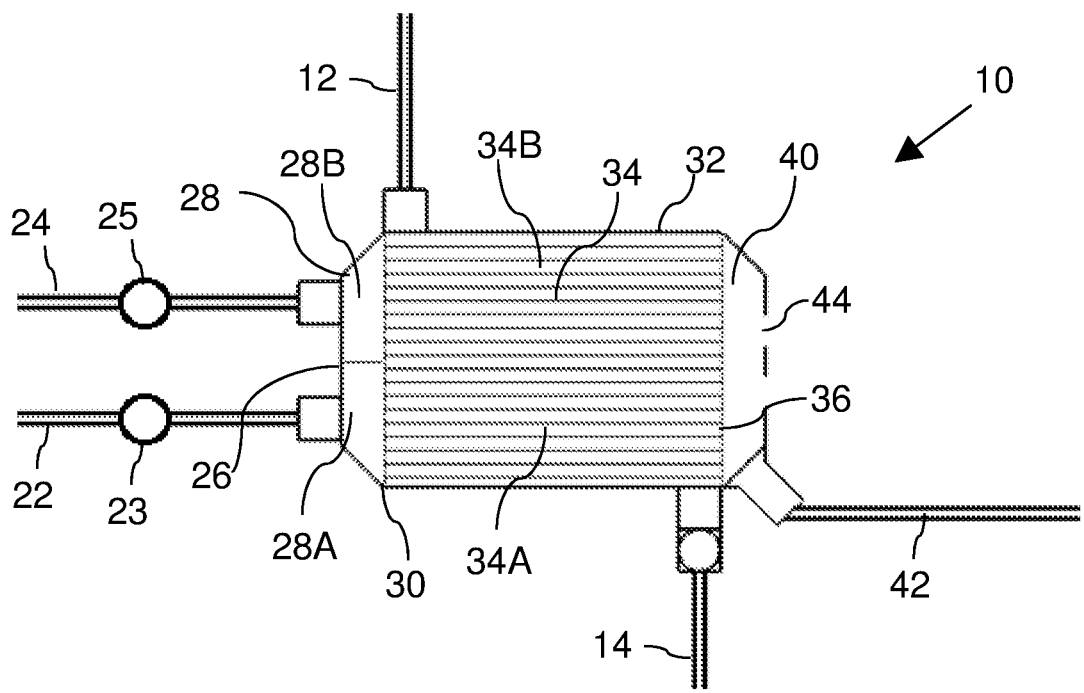
FIG. 2 is a schematic illustration of an oxygenator embodiment.

FIG. 2 shows an oxygenator 10 in accordance with embodiments of the invention. The oxygenator 10 comprises a blood inlet 12 and a blood outlet 14 providing a blood passage through the oxygenator 10. The oxygenator 10 comprises a first sweep gas supply 22 with a first sweep gas flow controller 23 and a second sweep gas supply 24 with a second sweep gas flow controller 25. The first and second sweep gas supplies 22 and 24 lead into a gas inlet zone 28 of the housing. The gas inlet zone 28 is fluidly connected with a gas-blood interface 32, which comprises a plurality of hollow fibres 34. For this reason, the oxygenator 10 is also referred to as a membrane oxygenator. The hollow fibres 34 are gathered at the gas inlet end by inlet-facing potting 30 constituting a gas interface border and at the gas exhaust end by outlet-facing potting 36. The gas passage leads from the gas inlet zone 28 via the hollow fibres 34 to an exhaust zone 40 downstream of the gas-blood interface 32 from where an exhaust gas line 42 extracts the gas. The oxygenator 10 comprises a housing that is gas tight at the gas inlet zone 28, to avoid contamination of the oxygenation gas. At the other end, at the exhaust zone 40, the housing comprises several openings 44 to allow pressure equilibration with the environment, in order to avoid a pressure build-up within the gas-blood interface 32. The blood passage between the blood inlet 12 and the blood outlet 14 is provided by the gas-blood interface 32 bounded by the inlet-facing potting 30 and the outlet-facing potting 36, and constituted by the volume outside the hollow fibres 34. The area between the potting 30 and 36 provides a gas-blood interface chamber.

Within the gas inlet zone 28 the oxygenator 10 comprises a partition 26 that at least partially separates the gas inlet zone into two compartments, a first gas inlet compartment 28A and a second gas inlet compartment 28B, each compartment constituting a section of the gas inlet zone. Each gas inlet compartment 28A, 28B can be considered as adjoining a different portion of the inlet-facing potting 30. As such, each gas inlet compartment has a different border with the gas-blood interface 32. Some hollow fibre bundles connect into the first gas inlet compartment 28A and are supplyable by gas from the first gas inlet compartment 28A. These hollow fibres are illustrated in FIG. 2 as first group of hollow fibres 34A. Likewise, a set of second group of hollow fibres 34B is fluidly connected with the second gas inlet compartment 28B.

The partition 26 is illustrated in a fixed position in FIG. 2. The partition 26 may be fixed in position, e.g. according to an oxygenator moulding design, an example of which is described below with reference to FIGS. 11 to 14. The partition 26 may be re-positionable at different locations. A re-positionable partition allows the number of fibres to be changed that may be supplied via the first gas inlet compartment 28A or via the second gas inlet compartment 28B. The partition 26 may be moveable across the potting 30. This allows the ratio of the number, and thereby the area of, the first group of hollow fibres 34A relative to the second group of hollow fibres 34B to be dynamically altered. The partition 26 may not necessarily have to seal against the potting because a small amount of gas seeping into the respective other area (for instance from the first gas inlet compartment 28A into the second hollow fibre membrane 34B) may be tolerable. Also, the hollow fibres are densely packed, and the edge of the partition 26 may be larger than a hollow fibre diameter. An edge of a partition in contact with the inlet-facing potting 30 may cover a certain amount of hollow fibres such that partition-covered hollow fibres are not practically supplyable by either the first or second gas inlet compartment. Conversely, if the partition 26 is not in close contact with the inlet-facing potting 30, hollow fibres just beneath the partition may be supplyable by both gas inlet compartments.

In FIG. 2, the partition 26 is located such that the first sweep gas supply 22 leads into the first gas inlet compartment 28A and the second sweep gas supply 24 leads into the second gas inlet compartment 28B. Each sweep gas supply is controllable separately by the respective sweep gas flow controllers 23 and 25. A larger number of sweep gas supplies may be provided, corresponding to the number of gas inlet compartments. Each sweep gas supply may be controllable separately. The sweep gas is understood to have a composition in which it is intended to be supplied to the gas-blood interface.

Figure 3:
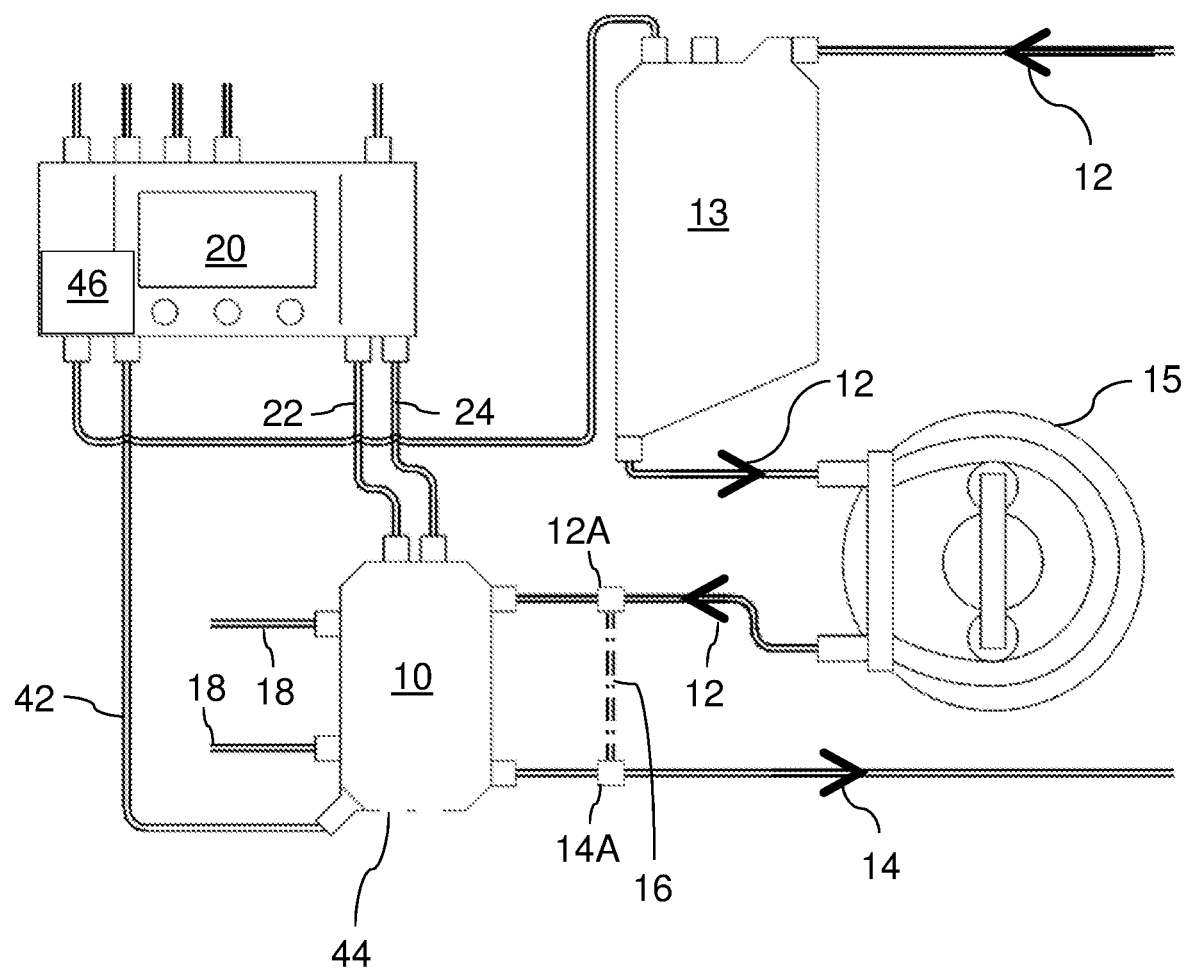
FIG. 3 is a schematic illustration of an extracorporeal perfusion system comprising an embodiment.

FIG. 3 illustrates an extracorporeal perfusion system comprising the oxygenator 10. In FIG. 3, no hollow fibres are indicated inside the oxygenator 10, to simplify the illustration, and some connections (blood inlet 12 and blood outlet 14) are positioned differently, but it will be understood the oxygenator 10 of FIGS. 2 and 3 can be identical. Likewise, other oxygenator embodiments of the invention may be used with the extracorporeal perfusion system. Venous blood flows via a blood inlet 12 into a venous blood reservoir 13 from where the blood is pumped via a pump 15 towards the oxygenator 10. The venous blood 12 may change in condition when passing the blood reservoir 13 and the pump 15, and may be provided with agents. For the purposes of the present specification, the venous blood is blood intended to be provided to the oxygenator 10 in order to be oxygenated and to have its carbon dioxide content reduced. In the oxygenator 10, the blood is exposed to oxygenation gas and exits via the blood outlet 14. A gas supply 20 is configured to supply oxygenation gas via a first sweep gas supply 22 towards the oxygenator 10. FIG. 3 also shows a second sweep gas supply 24 to provide oxygenation gas to the oxygenator 10. Furthermore, the oxygenator 10 is connected to a temperature control liquid 18. After the gas exchange, gas leaves the oxygenator 10 via the exhaust gas line 42. The exhaust gas flow is controlled by a gas extractor 46, which may be a low-pressure source. The low-pressure source creates an exhaust gas flow sufficient to promote a flow from the gas inlet zone 28 to the exhaust zone 40. For practical purposes, when assessing the oxygenator gas-blood exchange dynamics, the flow-inducing pressure gradient is usually considered negligible and often the pressure profile across the oxygenator 10 is considered constant as much as practically achievable. The pressure in which the oxygenator 10 operates is atmospheric, particularly as the housing of the oxygenator 10 at the exhaust side comprises openings 44 providing auxiliary vents. For the purposes of the present description in relation to oxygenator 10, incoming blood is provided via the blood inlet 12 towards the oxygenator 10, and outgoing blood is removed from the oxygenator via the blood outlet 14.

FIG. 3 shows an optional blood passage, namely a veno-arterial shunt 16 that provides a fluid connection directly from the blood inlet 12, via a shunt offtake 12A, to the blood outlet 14, via a shunt-merging location 14A, bypassing the oxygenator 10. If the veno-arterial shunt 16 is closed, blood passes through the oxygenator 10 as if no shunt 16 was provided. If the veno-arterial shunt 16 is open, this allows a portion of venous blood to bypass the oxygenator, in order to be mixed with blood that has been oxygenated. The veno-arterial shunt 16 is provided with a flow-controller allowing the amount of venous blood bypassing the oxygenator 10 to be controlled. This allows a ratio to be set between oxygenator-treated blood and unoxygenated blood, whereas the expression "unoxygenated" is used herein to define venous blood that, in a given cycle, bypassed the gas-blood interface and was not exposed to oxygenation gas. The veno-arterial shunt flow controller may be a pump or a flow restricting means. The veno-arterial shunt may comprise back-flow prevention means. The veno-arterial shunt flow may be effected by the pump 15 of the perfusion system when the veno-arterial shunt 16 is open to permit flow of blood bypassing the oxygenator 10. The shunt flow controllers may be gradually actuatable flow controllers, such as pumps or clamps.

FIGS. 4 to 9 show variants of the oxygenators 10, 10A and 11, and show various modes of operation of these oxygenator variants. Similar elements of the oxygenators 10, 10A and 11 are identified by the same numerals in FIGS. 2 and 4 to 9, and for brevity the description of corresponding parts is not repeated for every Figure.

Figure 4:
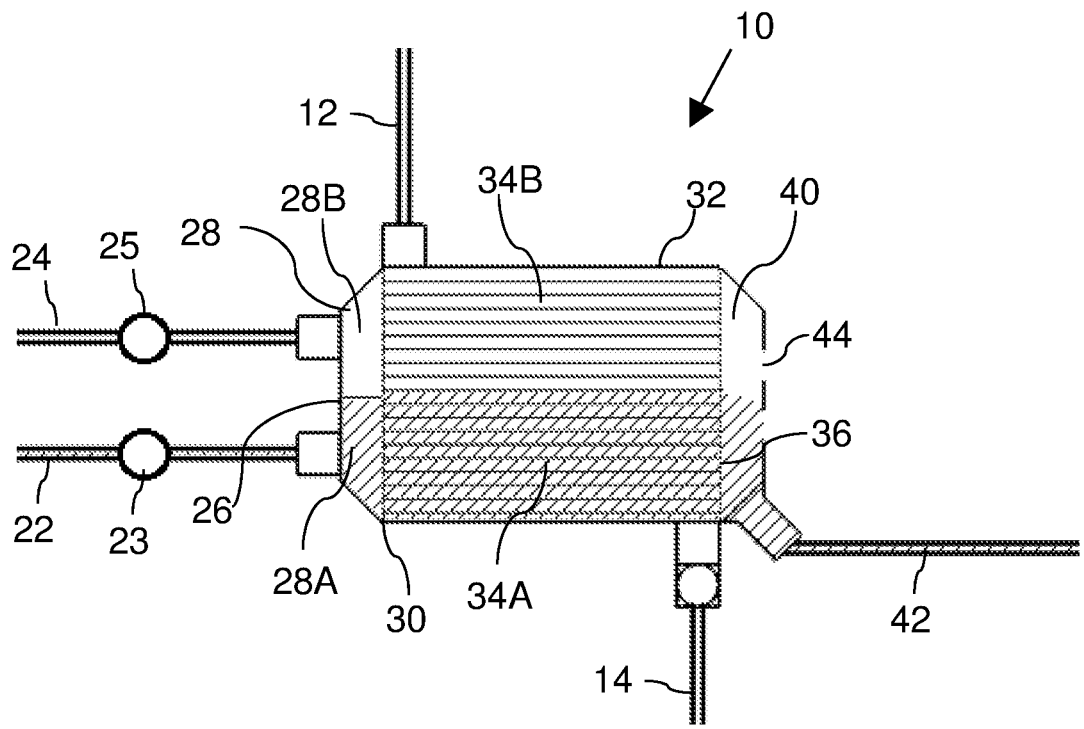
FIG. 4 is a schematic illustration of the FIG. 2 embodiment in one mode of operation.

FIG. 4 shows a first mode of operation in which sweep gas is supplied via the first sweep gas supply 22 only. The first sweep gas flow controller 23 is open. The second sweep gas flow controller 25 is closed. Thereby, sweep gas is supplied to the first group of hollow fibres 34A in fluid connection with the first gas inlet compartment 28A. The gas flow is indicated in by hatched lines. It is understood the hatched lines are merely illustrative to conceptually visualise the expected gas flow routes. The second group of hollow fibres 34B is not supplied by sweep gas, because the partition 26 impedes, or—depending on configuration—shuts off, the gas flow from the first gas inlet compartment 28A towards the second group of hollow fibres 34B. At the exhaust zone 40, exhaust gas is extracted via the extractor 46 (see FIG. 3;

not shown in FIG. 4) and so the gas is drawn away from the second group of hollow fibres 34B also from the exhaust end. It can be seen that the partition 26, in combination with the sweep gas supply control provides a gas distribution arrangement for the gas-blood interface. By way of the gas distribution arrangement, the gas flow conditions from the gas inlet zone to the exhaust zone can be provided in a heterogeneous manner, ie by design some portions of the gas-fluid interface are intentionally provided with differently conditioned oxygenation gas, or with different oxygenation gas conditions, than other portions. This is in contrast to the above-described situation of FIG. 1 in which the oxygenation conditions are homogeneous.

Figure 5:
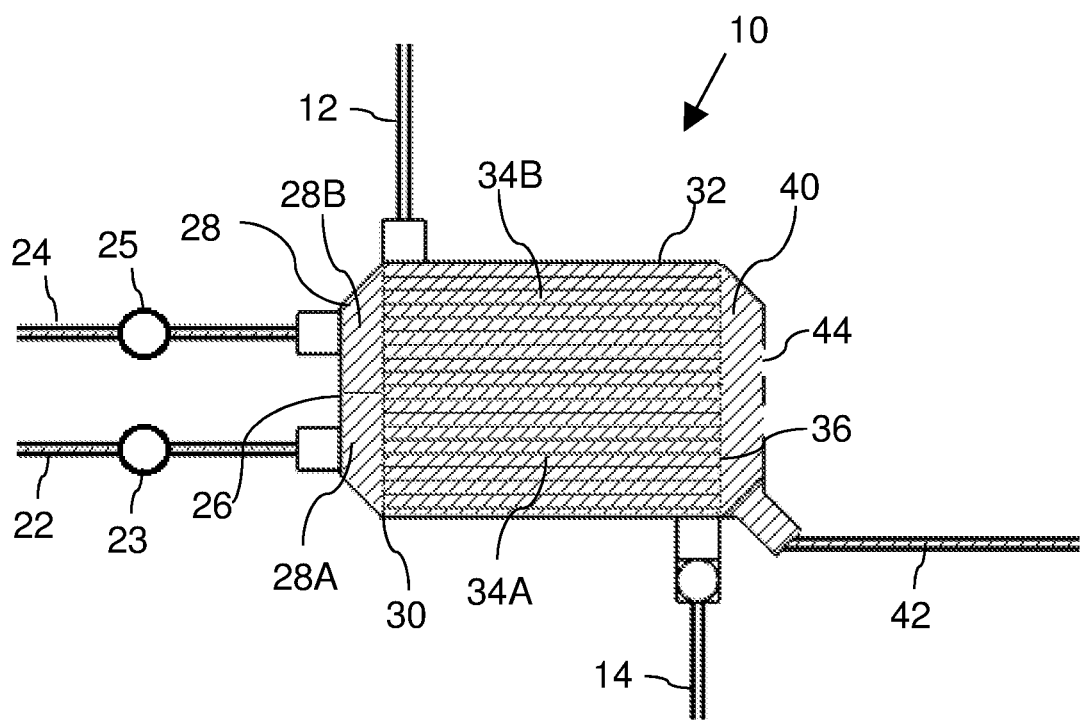
FIG. 5 is a schematic illustration of the FIG. 2 embodiment in another mode of operation.

FIG. 5 shows a second mode of operation in which sweep gas is supplied via both the first sweep gas supply 22 and the second sweep gas supply 24. Both sweep gas flow controllers 23 and 25 are open. The sweep gas flow is indicated by hatched lines and it can be appreciated that the second group of hollow fibres 34B is supplied with sweep gas. The sweep gas flow controllers 23 and 25 may be set to different flow rates. The oxygenation gas may have the same composition. For instance, the oxygenation gas may be originating from the same source. The oxygenation gas for the first sweep gas supply 22 may be of different composition than the oxygenation gas for the second sweep gas supply 24. For instance, different sources may be used for the sweep gas supplies. Likewise, the same source may be used and one sweep gas supply comprises an additional intake for a supply gas component (or one or more, in the case of more than two sweep gas supplies). The provision on a common exhaust line 42 facilitates the measurement and/or control of the total gas flow across the oxygenator 10.

Figure 6:
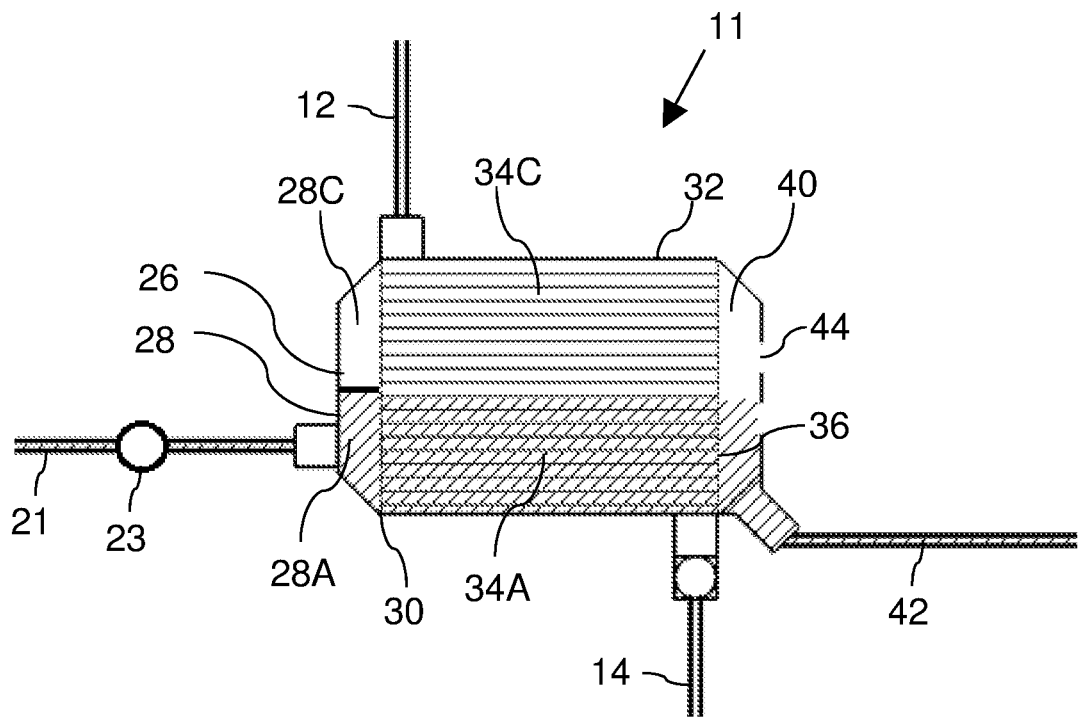
FIG. 6 is a schematic illustration of another embodiment in one mode of operation.

FIG. 6 shows an oxygenator 11 that is supplied by a single gas inlet, illustrated as a gas inlet 21. The gas inlet 21 provides sweep gas to the gas inlet zone 28, which is separated by a partition 26 into a first gas inlet compartment 28A and a further compartment 28C. The further compartment 28C is not directly supplied by oxygenation gas. Similar to what is shown in FIG. 4, only the first group of hollow fibres 34A of the gas-blood interface 32 is in fluid connection with the first gas inlet compartment 28A and therefore supplied by oxygenation gas. The remaining hollow fibres 34C of the gas-blood interface 32 is in fluid connection with the further compartment 28C and are not supplied by oxygenation gas. As mentioned before, the partition 26 may not necessarily provide a completely gas-tight seal with the potting 30. In that case, some oxygenation gas may, in practice, pass from the first gas inlet compartment 28A past the separation 26 into the further compartment 28C, and from there oxygenation gas may be extracted through the remaining hollow fibres 34 to the exhaust line 40. The amount of oxygenation gas passing into the further compartment 28C is considered negligible, if at all measurable.

Figure 7:
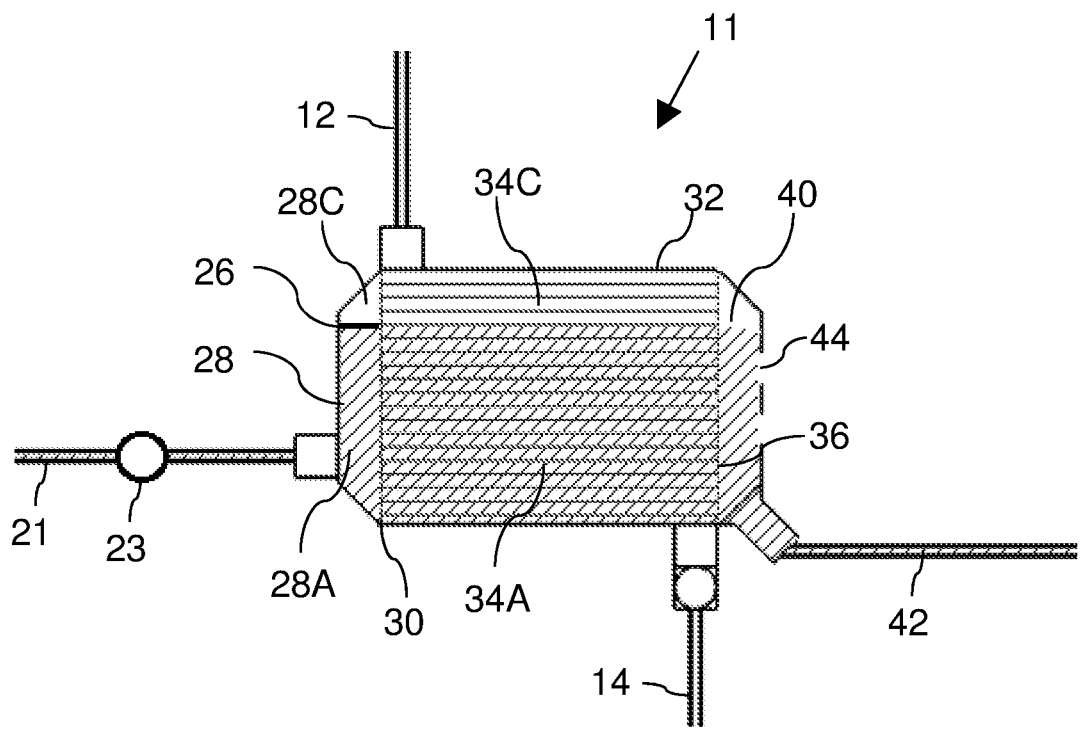
FIG. 7 is a schematic illustration of the FIG. 6 embodiment in another mode of operation.

FIG. 7 shows the FIG. 6 oxygenator 11 with the partition 26 moved to thereby increase the first gas inlet compartment 28A. This increases the interface area on the potting 30 between the first gas inlet compartment 28A and the hollow fibres, such that a larger number of hollow fibres are comprised in the first group of hollow fibres 34A. It is understood that, conversely, the partition 26 is movable to decrease the size of the first gas inlet compartment 28A and the corresponding number of fibres in the first group of hollow fibres 34A.

The size, or ratio, between the compartments may differ from what is shown in the examples herein. For instance, the first gas inlet compartment 28A may be dimensioned such that the ratio of the number of fibres of the first group of hollow fibres 34A to the second group of hollow fibres 34B is about 1:1, or about 1:2, about 1:3, or the inverse ratios. In a 1:2 arrangement, a supply via the first sweep gas supply 22 will provide oxygenation gas to about ⅓ of the hollow fibres.

FIGS. 4 to 7 show one partition 26 to separate the gas inlet zone into two compartments. Different numbers of gas inlet compartments may be provided, e.g. three, four, five or more gas inlet compartments. Each one of the compartments may be supplied by a separate inlet gas supply. The inlet gas supply may be separate for each supply, for instance such that each inlet gas supply may have a different composition and different flow rate. The inlet gas supply may use the same gas source and branch into a manifold with two or more supply branches each with individual flow control. In that case, each branch will provide sweep gas of the same composition but the flow rate of the sweep gas through each branch to each compartment can be controlled individually.

For instance, the gas inlet zone may be divided into six gas inlet compartments. The sweep gas may be supplied from a single source via a manifold providing a separate gas inlet to each one of the chambers, wherein each gas inlet comprises a separate gas flow control. If, in the six-compartment example, each compartment has the same size contact area with the potting 30, then each compartment can be used to supply one sixth of the hollow fibres. Such an arrangement would allow supplying an area in increments of ⅙th of the total hollow fibre area without requiring a moveable partition. It can be seen that this type of arrangement would easily allow a separation of the total hollow fibre area into separately supplyable regions of several different ratios without requiring a moveable part within the gas inlet zone. To provide examples, the regions could be either of same or of different size, such as 2:1 (two compartments of different size), 1:1:1 (three compartments of same size), 2:1:1:2 (four compartments allowing splitting the supplied area into two halves or three thirds), etc. Initial calculations indicate that separating the gas inlet zone into two separately supplyable regions, either in a 1:1 or 2:1 ratio, provide a sufficient degree of oxygenation control while also reducing the design effort required to provide two separate sweep gas supply channels.

The oxygenator 10 has a common exhaust line 42 which suffices to move oxygenation gas from the exhaust chamber 40, and therefore from all hollow fibres 34 joining into the exhaust chamber 40. Embodiments may comprise separately controllable exhaust lines for each group of hollow fibres.

In the arrangements shown above, blood flows from the blood inlet 12 via the hollow fibres from both groups 34A and 34B whether or not all hollow fibres are supplied by oxygenation gas. Thereby different interface regions are arranged successively in the blood flow direction of blood directed through the gas-blood interface constituted by the groups 34A and 34B of fibres. By way of the arrangement shown in FIGS. 2 and 4-7, blood directed through the gas-blood interface passes each one of the different interface regions. As illustrated in FIGS. 2 and 4-7, the gas-blood interface extends continuously within the blood passage. For the avoidance of doubt, blood flows, in the reading orientation of the Figures, from the top down, passing the second group of hollow fibres 34B before the first group 34A. As such, gas exchange is allowed to occur between the blood and the atmosphere inside the hollow fibres, including the second group of hollow fibres 34B, whether or not these are supplied with oxygenation gas.

Blood passing fibres that are not supplied by oxygenation gas still experiences a gas exchange with gas in the hollow space inside the fibre walls. However, because there is no atmosphere saturated with oxygen or nitrogen from the oxygenation gas, the partial pressures favour a diffusion of nitrogen gas from the blood into the fibre inside.

Water may condense inside the hollow fibres in an amount sufficient to block fibres. Such condensate can be removed by briefly increasing the gas flow rate (a so-called "sighing"). Any oxygen supplied into the fibres during sighing will be removed quickly via the exhaust line 42. For practical purposes, due to the relative flow volumes and transit times, a sighing procedure does not affect the partial gas pressures in the blood.

Figure 8:
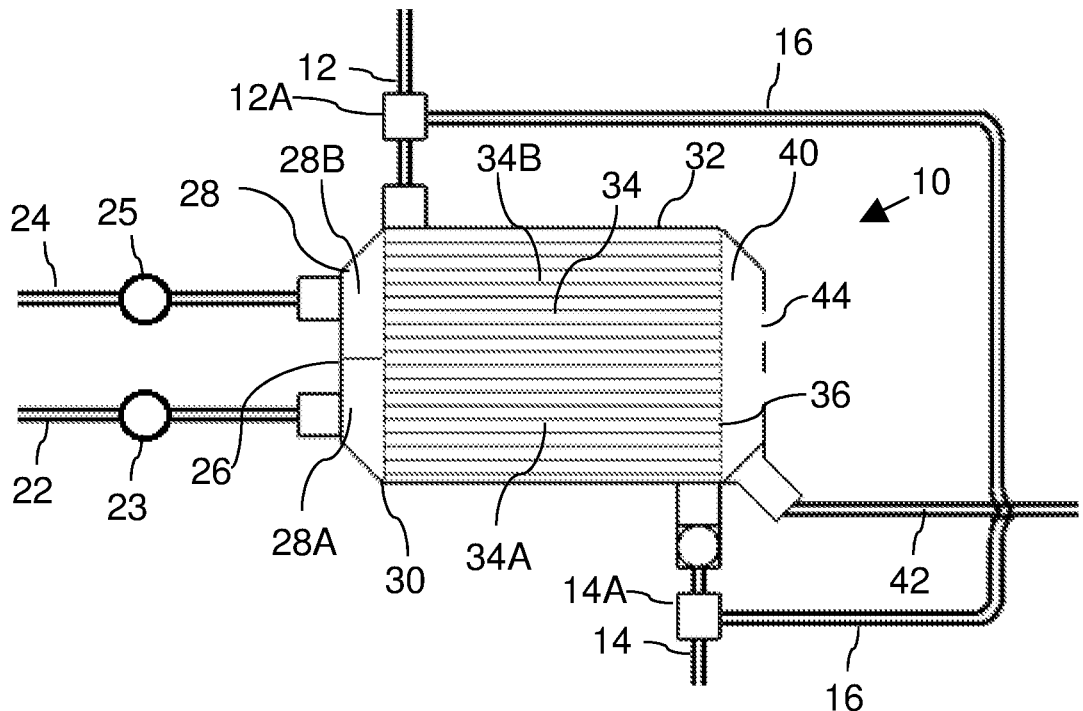
FIG. 8 is a schematic illustration of a part of the FIG. 3 arrangement.
Figure 9:
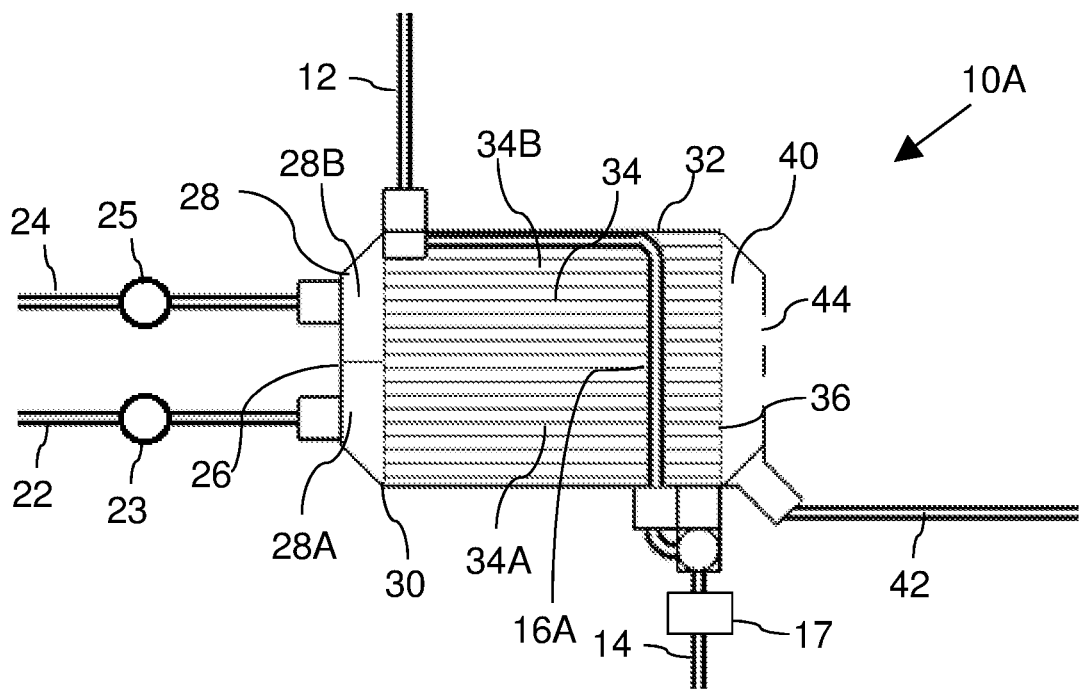
FIG. 9 is a schematic illustration of another embodiment.
Figure 10:
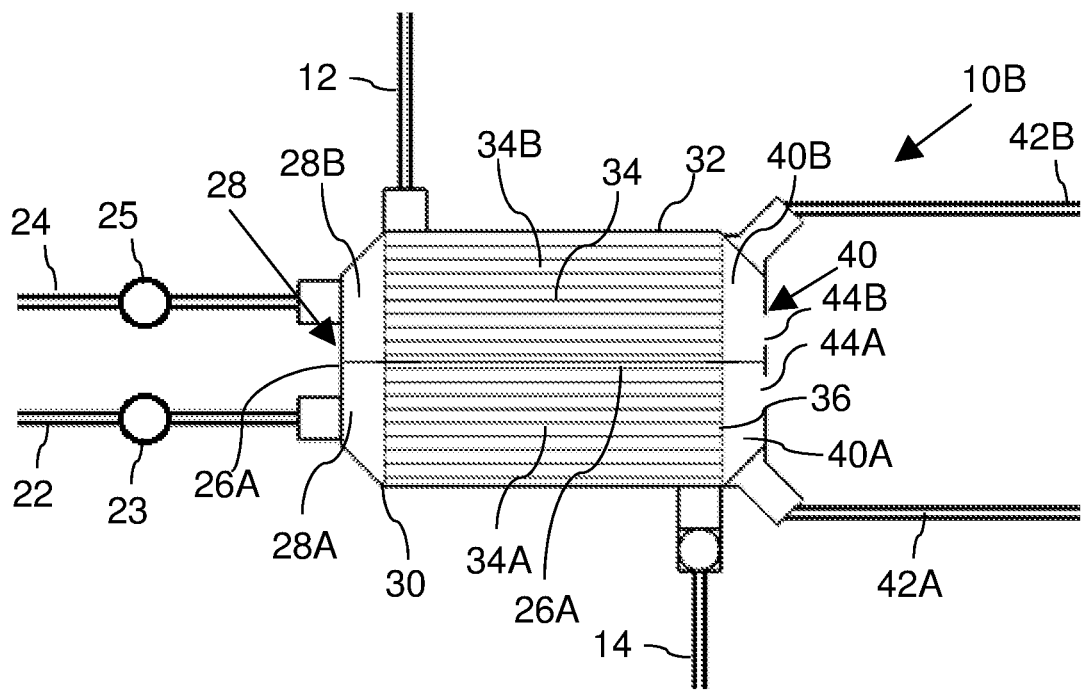
FIG. 10 is a schematic illustration of another embodiment.

FIGS. 8 and 9 show the oxygenator 10 and a variant of an oxygenator 10A. Corresponding elements of the oxygenators of FIGS. 9 and 10 are identified by the same numerals in FIGS. 2 and 4 to 7, and not described separately.

FIG. 8 shows the oxygenator 10 of FIG. 2 and, in context, the veno-arterial shunt 16 similar to that of FIG. 3, bypassing the oxygenator 10 between the blood inlet 12 and the blood outlet 14. The veno-arterial shunt 16 passage is not integral with the oxygenator 10. As described with reference to FIG. 3, the veno-arterial shunt 16 may be gradually opened or closed. The veno-arterial shunt 16 may be operated by a flow controller and flow sensing means to allow a closed loop control that is functionally coupled with flow control system of the oxygenator 10. As such, an embodiment may provide a system of an oxygenator and a veno-arterial shunt. The provision of a veno-arterial shunt allows venous blood that is unoxygenated (untreated by the gas-blood interface) to be mixed with oxygenator-treated blood to provide mixed blood. It will be understood that the properties of the mixed blood, such as relative concentrations of components such as PaO2, PaCO2, and properties such as temperature, depend on the respective properties of the oxygenator-treated blood and the unoxygenated blood and the ratio of the oxygenator-treated blood relative to the unoxygenated blood. As an example, if the oxygenator-treated blood is hyperoxic (has too high an oxygen content), mixing with a requisite amount of venous blood, which is lower in oxygen, reduces the oxygen content of the mixed blood. As such, the mixing of oxygenator-treated blood with unoxygenated blood allows a reduction of the oxygen percentage to below hyperoxic conditions.

FIG. 9 shows an oxygenator 10A that corresponds in many aspects to the oxygenator 10 of FIGS. 2 and 8, as indicated by the same reference numerals. The oxygenator 10A comprises a veno-arterial shunt 16A that is integral with the oxygenator 10A. The veno-arterial shunt 16A is gas-isolated from the gas passage, in particular from the gas-blood interface 32, and so the blood passing through the veno-arterial shunt 16A has no gas exchange with the oxygenation gas or any other atmosphere in the oxygenator. Venous blood shunted through the oxygenator 10A bypasses the oxygenation mechanism and can be made available as unoxygenated blood in order to be mixed with oygenator-treated blood that has been oxygenated.

The veno-arterial shunt 16A may follow a path that is at least partially or fully inside the oxygenator housing or that is at least partially or fully outside the oxygenator housing. The veno-arterial shunt 16A may follow a path that leads at least partially or fully through the gas-blood interface 32, or around the gas-blood interface but within the oxygenator housing. The veno-arterial shunt 16A may be integral with the oxygenator 10A in the sense that a single connector is required to connect the oxygenator 10A to the incoming blood line, and a single connector is required to connect the oxygenator 10A to the outgoing blood line, and a veno-arterial shunt is supplied via an internal diversion. This reduces the number of connections to be set up by clinical staff. The oxygenator 10A may comprise a holding channel or mixing area 17 downstream of the gas-blood interface in which thorough mixing of the oxygenator-treated blood and oxygenator-shunted blood is facilitated. The mixing area 17 may be inside the oxygenator housing or outside the oxygenator housing. Providing a veno-arterial shunt within the oxygenator allows the temperature control of the unoxygenated blood to be integrated with the oxygenator.

The oxygenation system may comprise a blood gas sensor arrangement to monitor blood gases of interest, such as blood oxygen and carbon dioxide, at locations upstream of the oxygenator, downstream of the oxygenator, and/or upstream and/or downstream of the veno-arterial shunt 16, in particular upstream and downstream of the shunt-merging location on the blood outlet 14. This allows the blood gas values to be monitored upstream of the oxygenator, of oxygenator-treated blood before it is mixed with unoxygenated blood, and of mixed blood comprising oxygenator-treated blood and shunted blood. In combination with oxygenator flow controllers and shunt flow controllers, the blood gas sensors allow a closed loop control to be provided that allows a blood gas component to be modulated to a precise set point. For instance, the set point may be a PaO2 level. If oxygenator-treated blood is hyperoxic, the amount of venous blood required to reduce the hyperoxic condition to a target condition can be derived from the blood gas values of the venous blood. Likewise, the blood gas values of the sensed blood allow a feedback loop to be provided to either increase the amount of oxygenator-treated blood or of shunted blood.

Likewise, the oxygenation system may comprise a temperature sensor arrangement to monitor the temperature of the blood at locations upstream of the oxygenator, downstream of the oxygenator, upstream and/or downstream of the veno-arterial shunt 16, and upstream and/or downstream of the shunt-merging location on the blood outlet 14. This provides a better degree of temperature control of the mixed blood. For instance, without a temperature control for the mixed blood, if the unoxygenated blood is warmer than desired and oxygenator-treated blood has a required temperature (set by temperature control liquid 18, see FIG. 3), the temperature of the mixed blood may be correspondingly above the set point for oxygenator treated blood. In that example, a closed loop control provides a mechanism that would allow the temperature control liquid to be modulated to take into account a mix with unoxygenated blood such that the mixed blood has a temperature as intended.

The veno-arterial shunt allows the oxygenator to be supplied by a sweep gas amount that would otherwise contain too much oxygen to avoid hyperoxic conditions. This provides, in turn, an opportunity to the modulate sweep gas flow rate in order to modulate the carbon dioxide content of the outgoing blood. Furthermore, by knowing the carbon dioxide concentrations of the venous blood, and the ratio or amounts of the unoxygenated (shunted) blood relative to the oxygenated blood, the sweep gas flow rate can be modulated to achieve a desired content of the outgoing blood. As a very simplified example, the sweep gas flow rate could be modulated to set a carbon dioxide concentration that would be too low in the oxygenator-treated blood, but that will be close to a desired set point after the oxygenator-treated blood has been mixed with the shunted blood.

Thereby, the shunt 16 and the shunt 16A provide a mechanism to reduce the risk of the blood provided from the oxygenator being hyperoxic.

The oxygenator 10 allows oxygenation gas to be provided that comprises a higher concentration of oxygen than would normally be used. Conventional sweep gas is comprised of oxygen in the region of 21% and nitrogen in the region of 79%, similar to the composition of air. A higher oxygen percentage is used in membrane oxygenators only to the extent that this may be required to reach a desired level of partial pressure of oxygen in the arterial blood. If the oxygen percentage in the sweep gas exceeds that required to achieve the desired partial oxygen pressure in the arterial blood, this risks producing hyperoxic conditions, which are conditions in which the oxygen content of the blood supplied to a patient is higher than required, and this may potentially be detrimental to a patient.

On the other hand, a higher oxygen percentage in the sweep gas allows a lower percentage of nitrogen, of which a higher percentage would otherwise be required to achieve a required total gas pressure. However, nitrogen gas is a main source of gaseous microemboli (GME), or gas bubbles, forming and remaining in blood. This is because the nitrogen contained in the oxygenation gas impedes the removal of nitrogen gas from the blood processed in an oxygenator. This is due to partial pressures of nitrogen in the oxygenation gas compared to the partial pressures of nitrogen dissolved in blood plasma being similar, and practically equal, and so there is no diffusion gradient.

In this context, Great British patent application GB1705556.7, published as GB2531221A, by the present applicant discloses an oxygenation system that allows oxygenation to be performed under hypobaric, or sub-atmospheric pressures. This allows an oxygen percentage to be provided in the oxygenation gas that is higher than 21%, even close to 100% or practically pure oxygen, because the total oxygenation gas pressure under hypobaric conditions is not so high as to cause hyperoxia. At the same time, the relative pressures encourage a removal of nitrogen gas from the blood. However, operating oxygenators safely under hypobaric conditions is challenging and solutions to provide reliable, safe hypobaric oxygenation conditions are described in Great British patent applications GB1705556.7 and GB1708810.5, both by the present applicant and published as GB2531221A and GB2563062A.

The oxygenator arrangement described in the present specification allows an oxygen content in the oxygenation gas to be used that is higher than 21%, even close to 100% or practically pure oxygen, under normal atmospheric pressure conditions, while providing a mechanism to reduce the occurrence of, and practically avoid, hyperoxia.

The present invention is based on the appreciation that use of oxygenation gas without, or a lower, nitrogen content favours the removal of nitrogen from the blood, while still allowing a controlled oxygenation and carbon dioxide removal.

This is achieved by passing the oxygenation gas, which may be up to 100% oxygen, through only a portion of the hollow fibres. The practical effect of the arrangement is that the sweep-gas exposed area of the gas-blood interface is modulatable during operation of the oxygenator. Blood passes in a practically continuous flow via the non-oxygenated hollow fibres (e.g., the second group of fibres 34B indicated in FIG. 4) before it passes the oxygenated hollow fibres (e.g., the first group of fibres 34A). For instance, using an arrangement and operation mode such as that described in FIG. 4, in FIG. 4 blood is allowed to flow in a practically continuous manner into the oxygenator 10 from the upper part of the oxygenator past the second group of hollow fibres 34B before passing the first group of hollow fibres 34A and before exiting via the blood outlet 14. The partition 26 may be arranged to divide the first gas inlet compartment 28A from the second gas inlet compartment 28B at a ratio 1:1 (as shown in FIG. 4) or any other ratio, such as 1:2. In a 1:2 configuration, the first gas inlet compartment 28A allows ventilation of about ⅓ of the total number of hollow fibres 34. The second gas inlet compartment 28B allows ventilation of the remaining ⅔ of the hollow fibres 34B. The blood passing through these two areas of fibres, whether or not ventilated, is where gas exchange takes place. By using different flow rates for the first and second groups of hollow fibres 34A and 34B, and/or different oxygenation gas composition, different oxygen gradients and total gas gradients can be achieved. The flow rates through the first and second groups of hollow fibres 34A and 34B influence the carbon dioxide removal rates.

In the illustrated example, by limiting the total area of hollow fibres that are actively ventilated, the oxygenation uptake of the blood can be influenced, and the flow rate provides control of carbon dioxide removal rates.

In known oxygenator designs, the oxygenation rate is controlled by modulating the composition, mainly the ratio of oxygen to nitrogen, of the oxygenation gas, wherein care has to be taken not to induce hyperoxia to the point that is considered potentially detrimental. For instance, a continuous supply over time of pure oxygen in a conventional oxygenator design is very likely to cause hyperoxia at detrimental levels. In the arrangement described herein, the oxygenation rate can be influenced while using higher oxygen content, even 100% oxygen. It is also an option to modulate the oxygenation gas composition by adding carbon dioxide, or a carbogen gas mixture, but it is not necessary to use nitrogen in the oxygenation gas in order to provide a lower partial pressure of oxygen in the oxygenation gas. As such, with a lower nitrogen partial pressure of the gas supplied, or with negligible amounts of nitrogen supplied to the gas-blood interface, it is possible to achieve a better removal rate of dissolved nitrogen from the blood over time.

An estimated oxygen transfer rate can be calculated based on factors including, but not necessarily limited to, a patient's size, metabolic demand, and blood flow rate. If the estimated oxygen transfer rate is greater than the maximum oxygen transfer rate that can be achieved by a maximum gas flow of pure oxygen via the first sweep gas supply, the oxygenator 10 allows additional gas to be directed/diverted into the second group of hollow fibres 34B. The gas flow rates of the first and second sweep gas supply 22 can be modulated to achieve the desired carbon dioxide removal rate.

For example, while no oxygenation gas is supplied to the second group of hollow fibres 34B, venous blood, which has the lowest total partial pressures of gases in the blood due to the low oxygen partial pressure, is allowed to interact with the hollow fibres of the second group of hollow fibres 34B. In one example, with no, or practically no gas flowing through the second hollow fibre membranes 34B, gaseous microemboli (GME) present in the venous blood experience pressure gradient conditions that encourage their removal. The removal of GME occurs due to the gradient between the GME and the inside of the hollow fibres, as well as the physical pressure applied by the blood on the GME bubble as that bubble is pushed past the surfaces the hollow fibres. The blood may therefore contain a significantly reduced number of GME after passing through the second group of hollow fibres 34B prior to reaching the first group of hollow fibres 34A. When the blood passes the first group of hollow fibres 34A, as these are supplied with a high or pure oxygen content, the blood is oxygenated with a steeper oxygen partial pressure gradient. At the same time, the oxygenation gas, to the extent that it does not comprise a higher nitrogen partial pressure than the blood, does not promote the formation of GME.

In the described exemplary use of the arrangement, the opportunity for oxygenating the blood is in one mode of operation limited to the blood passing the first group of hollow fibres 34A. If the resultant blood oxygen pressure is not high enough, the present arrangement allows additional oxygenation gas to be supplied to the second group of hollow fibres 34B. The gas supply may be gradually increased. Likewise, the opportunity for removing carbon dioxide is a function of the total gas flow. If, in the described example, the carbon dioxide removal rate is insufficient despite maximal gas flow through the first group of hollow fibres 34A, the present arrangement allows additional oxygenation gas to be supplied to the second group of hollow fibres 34B. The composition and/or the flow rate of the second sweep gas supply may be different from that of the first sweep gas supply.

If a high oxygen content, or pure oxygen, is used for both groups of hollow fibres, and if a carbon-dioxide removal demand requires high flow rates through both membranes, this may result in a higher oxygenation value than the ideal oxygen target value. However, even if too high an oxygenation value is generated, this would be a temporary issue. The present arrangement allows a nitrogen partial pressure to be avoided while reducing the occurrence of hyperoxia conditions to less than would otherwise be the case if 100% oxygen was used as oxygenation gas for an entire oxygenator.

In such a situation, the provision of an veno-arterial shunt 16 or similar shunting path for venous blood allows the oxygen content of the outgoing blood to be reduced by mixing the oxygenator-processed blood with unoxygenated blood to provide mixed blood with lower oxygen content.

FIG. 10 shows an oxygenator 10B in accordance with embodiments of the invention. In FIG. 10, the same reference numerals are used as in FIGS. 2, 4 and 5 for similar components without repeating the specific description. Similarly to the oxygenator 10 illustrated in FIG. 2, the oxygenator 10B comprises a first sweep gas supply 22 with a first sweep gas flow controller 23 and a second sweep gas supply 24 with a second sweep gas flow controller 25. The first and second sweep gas supplies 22 and 24 lead into a gas inlet zone 28 of the housing. The gas inlet zone 28 is fluidly connected with a gas-blood interface 32, which comprises a plurality of hollow fibres 34 providing a gas exchange interface. The hollow fibres 34 are gathered at the gas inlet end by inlet-facing potting 30 constituting a gas interface border and at the gas exhaust end by outlet-facing potting 36. The gas passage leads from the gas inlet zone 28 via the hollow fibres 34 to an exhaust zone comprising two exhaust compartments 40A, 40B downstream of the gas-blood interface 32 from where a plurality (here two) exhaust gas lines 42A and 42B extract the gas. The oxygenator 10B comprises a housing that is gas tight at the gas inlet zone 28, to avoid contamination of the oxygenation gas. At the exhaust zone 40, the housing comprises several openings 44A, 44B to allow pressure equilibration with the environment, in order to avoid a pressure build-up within the gas-blood interface 32. The blood passage between the blood inlet 12 and the blood outlet 14 is provided by the gas-blood interface 32 bounded by the inlet-facing potting 30 and the outlet-facing potting 36, and constituted by the volume outside the hollow fibres 34. The area between the inlet-facing potting 30 and the outlet-facing potting 39 provides a gas-blood interface chamber 32.

Within the gas inlet zone 28 the oxygenator 10B comprises a partition 26A that at least partially separates the gas inlet zone into two compartments, a first gas inlet compartment 28A and a second gas inlet compartment 28B, each compartment constituting a section of the gas inlet zone. The partition 26A extends through the inlet-facing potting 30, through the hollow fibre bundles of the gas-blood interface 32, through the outlet-facing potting 36 and into the exhaust zone 40 to at least partially separate the exhaust zone 40 into two exhaust compartments 40A and 40B. Each gas inlet compartment 28A, 28B can be considered as adjoining a different portion of the inlet-facing potting 30. Likewise, each exhaust compartment 40A, 40B can be considered as adjoining a different portion of the outlet-facing potting 36. As such, each gas inlet compartment 28A, 28B and each exhaust compartment 40A, 40B has a different border with the gas-blood interface 32. Each exhaust gas line 42A and 42B is configured to extract gas from one of the compartments 40A, 40B, respectively. The exhaust gas lines 42A and 42B may join into a common exhaust gas flow control system.

By way of the continuously extending partition 26A, individual fibre channels connect only their respective inlet and exhaust compartments, i.e. fibre channels supplied from the first gas inlet compartment 28A lead into the first exhaust compartment 40A and fibre channels supplied from the second gas inlet compartment 28B lead into the second exhaust compartment 40B. Thereby, it can be avoided that fibre channels supplied from one inlet compartment connect to different exhaust compartments, or that fibre channels supplied from different inlet compartments connect to the same exhaust compartment. A group of hollow fibre bundles connects into the first gas inlet compartment 28A and is supplyable by gas from the first gas inlet compartment 28A. These hollow fibres are illustrated in FIG. 10 as first group of hollow fibres 34A. Likewise, a second group of hollow fibres 34B is fluidly connected with the second gas inlet compartment 28B.

Figure 11:
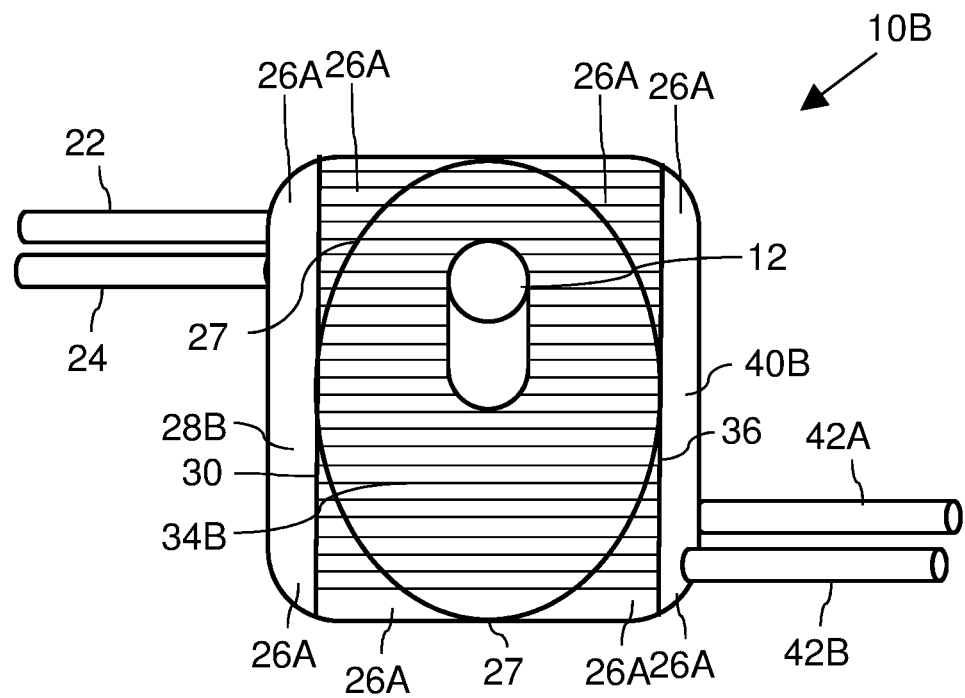
FIG. 11 is a schematic top view of the FIG. 10 embodiment.

FIG. 11 shows a schematic top view of the FIG. 10 illustration of the oxygenator 10B. From left to right in the reading orientation of FIG. 11, FIG. 11 shows the second sweep gas supply 24 above the first sweep gas supply 22 supplying the gas inlet zone, of which only the second gas inlet compartment 28B is visible in FIG. 11 (the first gas inlet compartment is understood to be, in the view of FIG. 11, beneath the second gas inlet compartment 28B). The gas passage leads via inlet-facing potting 30 via the gas-blood interface, of which only the second group of hollow fibres 34B is depicted in FIG. 11, via the outlet-facing potting 36 into the second exhaust compartment 40B. Two exhaust gas lines 42A and 42B are provided to draw exhaust gas from the respective exhaust gas compartments 40A and 40B. Illustrated beneath the second group of hollow fibres 34B is a continuous partition 26A extending from the gas inlet zone 28 through the inlet-facing potting 30, the gas-blood interface, the outlet-facing potting 36 and through the exhaust zone 40. By way of the continuous partition 26A, two different, separately supplyable gas exchange interface regions are provided. It will be understood that the gas passage beneath the partition 26A, consisting of the first inlet compartment 28A, the first group of hollow fibres 34A and the exhaust gas compartment 40A is not depicted in FIG. 11.

Figure 12:
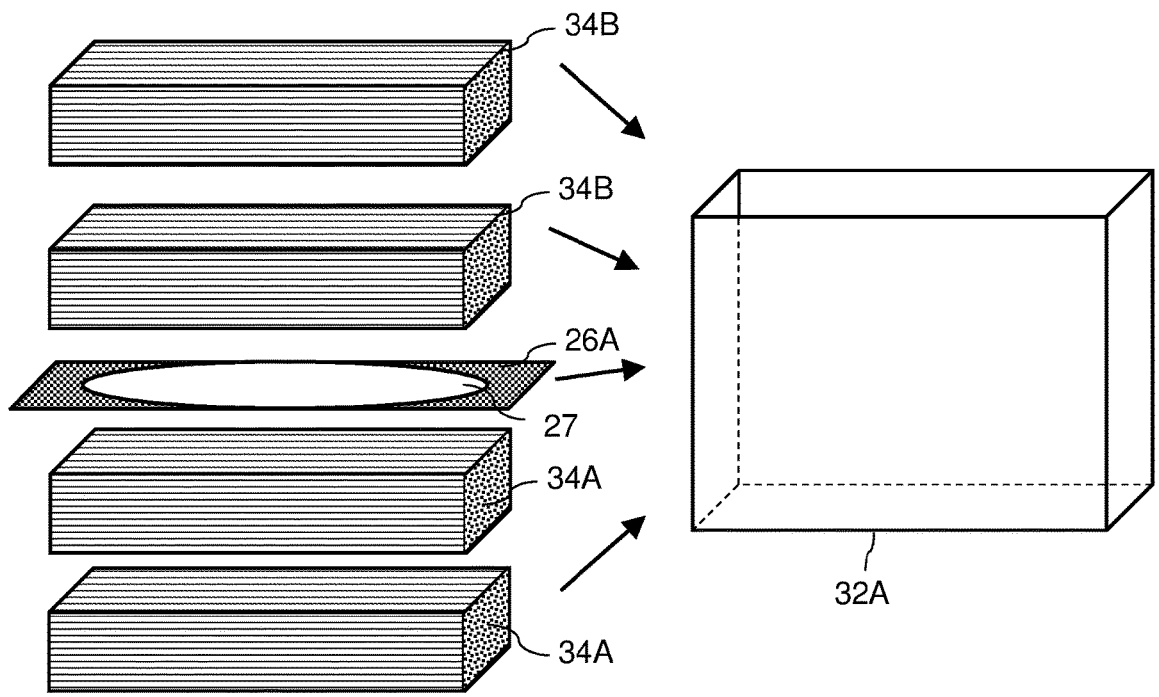
FIG. 12 shows a schematic exploded view of components used in embodiments.

To better illustrate the separation of groups of hollow fibres by way of a partition, FIG. 12 illustrates schematically an exploded view of components of the gas-blood interface 32. The hollow fibres are provided in bundled form, in the form of so-called "mats". FIG. 12 shows four such mats (two mats 34B and two mats 34A) although in practice, several tens of such mats, typically between 50 to 100 mats, may be used in an oxygenator assembly. Each mat 34A, 34B comprises a large number of hollow fibres that are to some extent intertwined such that it is not practically possible to identify the ends belonging to a particular fibre. Several of such mats are stacked to provide a common gas-blood interface. In order to provide a compartmented gas passage, as shown in FIGS. 10 and 11, a partition 26A is located between two sets of mats. Conceptually, in FIG. 12, the mats 34B above the partition 26A form the second group 34B of hollow fibres and the mats 34A below the partition 26A form the first group 34A of hollow fibres.

The partition 26A comprises a central aperture 27 illustrated generally in oval form. The partition material is less gas-permeable than the fibre membranes, and for practical considerations the partition material is gas-impermeable, such that it provides a gas-tight separation of the first and second groups 34A, 34B of hollow fibres. The partition 26A may be made from a suitable material, such as polycarbonate. The partition 26A may be integral with the oxygenator housing or with a component of the oxygenator housing. The edges of the central aperture 27 may be provided with a surface treatment such as a coating with blood-active properties. For instance, the edges may have a surface treatment providing anti-coagulant properties. In embodiments, the partition may be located in a manner avoiding contact with blood (see description in relation to FIG. 14).

FIG. 12 further shows a gas-blood interface container 32A into which the mats 34A and 34B, as well as the partition 26A are placed in stacked form.

Figures 13, 14:
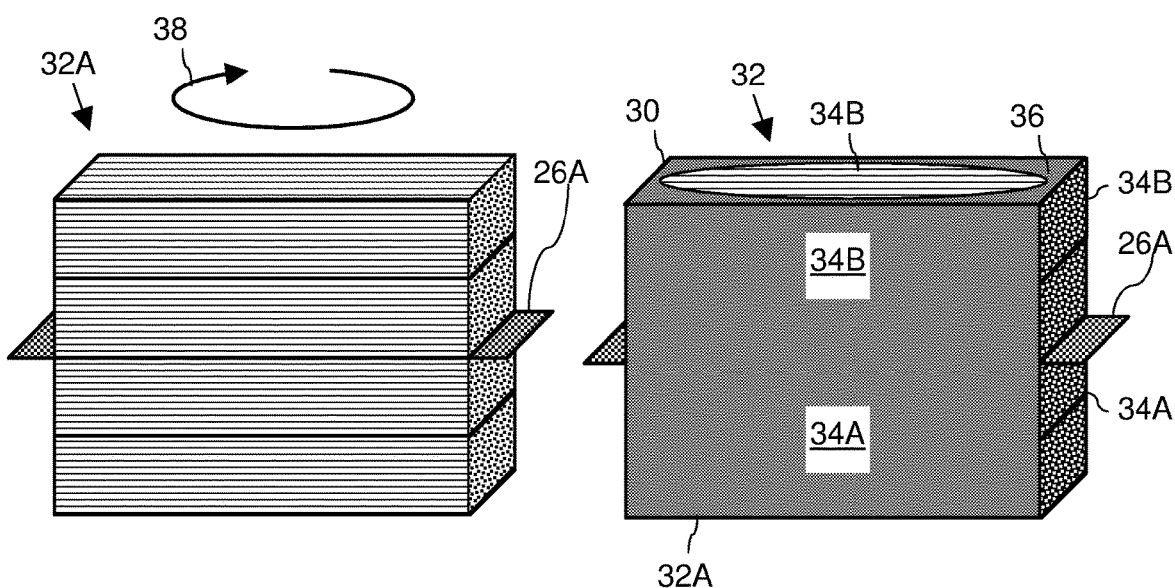
FIG. 13 shows a schematic assembly of the components of FIG. 12.
FIG. 14 shows a schematic component incorporating the assembly of FIG. 13.

FIG. 13 shows, schematically, an assembly comprising the gas-blood interface container 32A provided with a plurality (here: four) mats separated into groups (here: two) groups of hollow fibres 34B and 34A by a partition 26A. The partition 26A is in at least one dimension longer than the fibre mats such that portions of the partition 26A extend beyond the inlet end of the mats and/or beyond the outlet end of the mats. The partition 26A is negligibly thin in relation to the groups of mats and so there is practically no void between the groups of mats. The mats immediately above and below the partition 26A contact each other via the aperture 27.

The following arrangement describes how potting material may be provided to define a blood passage that avoids contact with partition components. The gas-blood interface container 32A may be provided with potting material by pouring or injecting potting material while the gas blood interface container is rotated (indicated by an arrow 38) to an extent sufficient to cause potting to solidify between the fibres in a cylindrical shape defined by centrifugal forces. In other words, if the gas-blood interface container 32A is rotated about a rotation axis, potting material will, while flowable, collect at the peraxial walls and corners of the gas-blood interface container 32A and a cylindrical hole, free of potting material, remains along the rotation axis. It will be understood that the gas-blood interface container may be provided with temporary or permanent container elements that contain the potting material before it sets. The potting material may set in the interstitial spaces between the individual fibres; and so the cylindrical hole provides a blood passage crossing fibres and the hollow space inside the fibres provides a gas passage from one fibre end to the other (here: opposite) fibre end.

FIG. 14 shows schematically the gas blood interface container 32A after potting material has been introduced in the manner described above and set, leaving a cylindrical channel, free of potting material, in which hollow fibres are exposable to blood. The hollow fibres are held in position in the potting material. The hollow fibres of different mats are provided as a practically homogenous gas-blood interface 32. The potting material may have set as an unitary component; nevertheless a portion of the potting material constitutes the inlet-facing potting 30. Another portion of the potting material constitutes the outlet-facing potting 36. The amount of potting material can be chosen such that the cross-section of the cylindrical channel is smaller than the aperture 27 in the partition 26A, such that no material of the partition 26A protrudes into the cylindrical channel. Consequently, such an arrangement avoids any contact of blood with the partition 26A during operation of the oxygenator. As such it will be understood that the partition and the aperture may have any other shape or configuration as long as this is suitable to maintain different groups of the gas-blood interface separated.

Once assembled into an oxygenator housing, the protruding portions of the partition 26A provide partitions of the gas inlet zone and/or gas exhaust zone, respectively. As such, while one or more partition structures are present, these may be understood as alignment structures for positioning of the partition in the inlet zone and/or outlet zone between the tightly packed hollow fibres. As illustrated, the partition may be arranged such that it does not interfere with the blood passage. Within the blood passage, the gas-blood interface is therefore uniformly distributed, practically indistinguishable in performance from a single continuous gas-blood interface arrangement.

Although the blood passage may have other shapes, a passage without corners, such as a cylindrical passage or a passage of oval section, avoids introducing flow patterns and avoids channel geometries in which blood clotting may be more likely to occur. The illustrated arrangement combines a linearly extending gas passage, which allows exhaust ends opposite the gas inlets, with a linear blood passage without dead zones.

It will be understood that the gas-blood interface 32 depicted in FIG. 14 is used as a component of an oxygenator, such as oxygenator 10B illustrated in FIGS. 10 and 11

As the central aperture 27 is larger than the profile of the blood passage, the central aperture provides an uninterrupted blood passage, allowing blood to pass around the hollow fibre bundles from the blood inlet 12 via the gas-blood interface 32 into the blood outlet 14 (not depicted in FIG. 11). By way of the central aperture 27, the fibre bundles of adjacent mats lie so close that the gas-blood interface within the blood passage is uniformly distributed from the second group of hollow fibres 34B to the first group of hollow fibres 34A. By uniformly distributed it is meant that to blood cells passing the blood passage, the different groups of hollow fibres provide practically the same flow conditions to blood cells passing between mats of the same group of fibres (34B or 34A) as to blood cells passing through the aperture 27. Thereby, the blood passage is configured as a continuous fibre interface region. A blood cell passing through the blood passage encounters a practically homogenous environment of fibre membranes exposing the blood cell to homogenous levels of shear stress.

The blood passage and gas-blood interface is contained in the same housing while a plurality of differently controllable gas-blood interfaces are separated by a partition 26A. While FIGS. 12 to 14 depict only one partition 26A separating the gas-blood interface approximately half-way, embodiments may comprise multiple partitions and/or may comprise different separations, e.g. to separate the gas-blood interface provided. The partition 26A may not necessarily have to be unitary if during manufacture of the oxygenator 10B it can be ensured that each gas passage remains separated. For instance, the partition 26A may be provided by a plurality of elements, such as plates or sheets of bracket or wedge shape. The shapes may comprise a cut-out constituting part of an aperture that can be combined to define a multi-component partition. The partition function may be provided by a plurality of components, for instance by strips located at the inlet end and at the outlet end only, between two groups of hollow fibres (e.g. between two mats). As such the partition 26A can be understood as a retaining structure that allows the partition of the gas inlet zone and/or of the gas exhaust zone to be held in a position clearly separating two gas passages. The partition 26A facilitates the strict separation of gas passages from the gas inlet zone through to the exhaust zone. The provision of a unitary partition component extending through the potting facilitates the assembly of a stacked arrangement, but it will be understood from FIG. 12 that multiple elements may be used. The examples in FIGS. 12 to 14 provide a configuration that shuts off gas flow from the first gas inlet compartment 28 towards the second group of hollow fibres 34B (and vice versa). This provides a much more precise control over the oxygenation properties and GME-removing effect.

As depicted in the Figures, the gas-blood interface 32 is comprised of linearly extending hollow fibres. A clear separation of gas passages may be achieved with other configurations, such as fibre loops positioned such that the gas inlet is next to the gas outlet in a side-by-side configuration, rather than opposite, with one or more partition structures separating two groups of fibres. While hollow fibres may be arranged differently, for instance wound, the provision of a linear gas-blood interface, with the exhaust practically opposite the gas inlet, has been found by the applicant to facilitate precise control of blood gas values using closed-loop feedback mechanisms.

The hollow fibres may be made from any suitable material, such as PMP and polypropylene. Although described with reference to hollow fibres, the invention may be provided with different gas-blood interface designs such as planar or corrugated sheets or webbing providing gas channels.

The oxygenator 10B described with reference to FIGS. 10 to 14 may be provided with a veno-arterial shunt 16 or 16A as described in relation to FIGS. 8 and 9, and may be used in an extracorporeal perfusion system as described in relation to FIG. 3.

FIG. 15 shows steps of an oxygenation method 50. The method comprises a step 52 of providing an oxygenator gas-blood interface that is separated into regions that are separately supplyable by sweep gas. The gas-blood interface may be separated into such regions by arrangements described above, such as a partition in the gas inlet zone and/or by providing different gas inlets. In step 54, sweep gas is supplied to at least one of the regions. This region could be supplied in the manner described above with reference to FIG. 4. In optional step 56, the sweep gas supply is modulated differently for each region. For instance, as described with reference to FIGS. 4 and 5, the gas supply 22 and 24 is modulated differently for the first and second groups 34A and 34B of hollow fibres. In optional step 58, the sweep gas supply is modulated by modulating the area of the gas-blood interface region. For instance, as described with reference to FIGS. 6 and 7, the partition 26 allows the area available for the gas-blood interface of the first group of hollow fibres 34A to be changed (increased and decreased). Both steps 56 and 58 may be carried out concurrently. In optional step 60, the PaO2 and/or PaCO2 of the outgoing blood are monitored. In optional step 62, the total gas flow rate is modulated. Steps 56 to 62 may be repeated until a blood value such as PaO2, PaCO2 or blood temperature, or two or more of these, reach a pre-determined set point. In particular, steps 56 to 62 may be provided in a closed loop allowing the blood values to be maintained at the pre-determined set point.

In optional step 64, a veno-arterial shunt is provided to allow a portion of venous blood to bypass the gas-blood interface. This could be provided in the form of the embodiments illustrated in FIGS. 3, 8 and 9. In optional step 66, venous blood (unoxygenated blood) is mixed with oxygenator-treated blood to provide mixed blood. As described above in relation to the veno-arterial shunt, the method may include measuring blood values and/or gas values and using these values in a control loop to modulate the amount of venous blood mixed with the oxygenator-treated blood.

The oxygenation system may comprise and/or be connected to a controller and software instructions implemented by the processor. Any of the method steps may be carried out by a controller.

The invention claimed is:

1. An oxygenator for an extracorporeal ventilation system, the oxygenator comprising:
 a gas passage and a blood passage arranged to allow gas exchange of an oxygenation gas supply with blood via a gas-blood interface, the gas-blood interface being separated into a plurality of interface regions, wherein the gas passage leads from a gas inlet zone via the gas-blood interface to a gas exhaust zone, and wherein the blood passage leads from a blood inlet via the gas-blood interface to a blood outlet and
 a supply gas distribution arrangement comprising:
  one or more partitions each in contact with an outer wall of the gas-blood interface to divide the gas inlet zone into a plurality of gas inlet sections, each gas inlet section having a border with a different interface region of the plurality of interface regions, and
  a plurality of gas inlet ports each configured to receive a separate inlet gas supply, a separate gas inlet port being provided for each gas inlet section thereby allowing the oxygenation gas supply to be modulated differently for different interface regions of the gas-blood interface,
 wherein the different interface regions are arranged successively in blood flow direction for blood directed through the gas-blood interface to pass each interface region, and wherein the gas-blood interface is uniformly distributed within the blood passage.

2. The oxygenator according to claim 1, wherein the supply gas distribution arrangement comprises one or more partitions each dividing the gas-blood interface in a plurality of gas-blood interface compartments.

3. The oxygenator according to claim 1, wherein the blood passage through the gas-blood interface comprises a circular or oval profile.

4. The oxygenator according to claim 1, wherein the gas passage extends linearly.

5. The oxygenator according to claim 1, comprising a blood sensor arrangement to obtain measurements representative of one or more blood values selected from a group comprising of incoming blood oxygen concentration, incoming blood carbon dioxide concentration, outgoing blood oxygen concentration, outgoing blood carbon dioxide concentration, and blood temperature.

6. The oxygenator according to claim 5, comprising a supply gas control configured to receive the one or more measurements representative of one or more blood values, and to modulate the flow rate and/or the composition of the oxygen gas supply gas in response to the measurements.

7. The oxygenator according to claim 1, comprising a gas sensor arrangement to obtain measurements representative of one or more gas values selected from a group comprising of oxygenation gas flow rate, oxygenation gas pressure, exhaust gas flow rate, exhaust gas pressure, exhaust gas oxygen concentration, and exhaust gas carbon dioxide concentration.

8. The oxygenator according to claim 7, comprising a supply gas control configured to receive one or more measurements representative of one or more gas values, and to modulate the flow rate and/or the composition of the oxygen gas supply gas in response to the measurements.

9. The oxygenator according to claim 1, comprising a veno-arterial shunt providing a diversion from the blood inlet to the blood outlet, the diversion bypassing the gas-blood interface, wherein the veno-arterial shunt allows a portion of incoming blood to be diverted to the blood outlet without exposure to the oxygenation gas supply.

10. The oxygenator according to claim 9, further comprising a shunt flow controller to control the amount of incoming blood diverted to bypass the gas-blood interface.

11. The oxygenator according to claim 10, configured to receive one or more measurements representative of one or more blood values and/or gas values, and to actuate the shunt flow controller to modulate the flow rate of blood diverted through the shunt passage in response to the measurements in order to maintain a blood value at a pre-determined set point.

12. The oxygenator according to claim 1, comprised in an extracorporeal ventilation system comprising one or more oxygenation gas supply lines each connected to the supply gas distribution arrangement.

13. The oxygenator according to claim 1, wherein the blood passage through the gas-blood interface is linear.

14. The oxygenator according to claim 1, wherein the gas-blood interface arrangement comprises hollow fibres comprising gas passage openings toward the gas inlet zone.

15. The oxygenator according to claim 14, wherein the oxygenator is configured to individually open and/or close the openings of one or more hollow fibres or one or more groups of hollow fibres.

16. A method for extracorporeal blood oxygenation and carbon dioxide control in an oxygenator, the method comprising:
providing an oxygenator comprising:
(i) a gas passage and a blood passage arranged to allow gas exchange of an oxygenation gas supply with blood via a gas-blood interface, the gas-blood interface being separated into a plurality of interface regions, wherein the gas passage leads from a gas inlet zone via the gas-blood interface to a gas exhaust zone, the blood passage leads from a blood inlet via the gas-blood interface to a blood outlet, the plurality of interface regions are arranged successively in blood flow direction, and the gas-blood interface is uniformly distributed within the blood passage; and
(ii) a supply gas distribution arrangement comprising one or more partitions each in contact with an outer wall of the gas-blood interface to divide the gas inlet zone into a plurality of gas inlet sections, each section having a border with a different region of the gas-blood interface, the supply gas distribution arrangement further comprising a plurality of gas inlet ports each configured to receive a separate inlet gas supply, a separate gas inlet port being provided for each gas inlet section; and
supplying sweep gas to the plurality of interface regions via the plurality of gas inlet ports, wherein supplying sweep gas comprises modulating the sweep gas differently for each of the plurality of interface regions.

17. The method according to claim 16, wherein each of the plurality of interface regions is exposed to sweep gas across a respective interface area, and wherein the method further comprises modulating the sweep gas by modulating one or more of the respective interface areas of the plurality of interface regions.

18. The method according to claim 16, further comprising monitoring partial pressure of oxygen of outgoing blood, partial pressure of carbon dioxide of outgoing blood, and/or temperature of outgoing blood.

19. The method according to claim 16, further comprising modulating the sweep gas flow rate.

20. The method according to claim 19, wherein the sweep gas flow rate is modulated repeatedly until at least one blood value reaches a pre-determined set point, wherein the at least one blood value is one or more of: partial pressure of oxygen of outgoing blood; partial pressure of carbon dioxide of outgoing blood; and/or temperature of outgoing blood.

21. The method according to claim 20, wherein the sweep gas flow rate is modulated repeatedly as part of a closed-loop control allowing the at least one blood value to be maintained at the pre-determined set point.

22. The method according to claim 16, further comprising providing a veno-arterial shunt to allow a portion of venous blood to bypass the gas-blood interface.

23. The method according to claim 22, further comprising mixing venous blood with oxygenator-treated blood to provide mixed blood.

24. The method according to claim 23, further comprising measuring blood values and/or gas values of the venous blood, the oxygenator-treated blood, and/or the mixed blood and using the blood values and/or the gas values in a closed-loop control to modulate the amount of venous blood mixed with the oxygenator-treated blood.

* * * * *